United States Patent
Hell et al.

(10) Patent No.: US 7,538,893 B2
(45) Date of Patent: May 26, 2009

(54) METHOD OF MICROSCOPICALLY EXAMINING A SPATIAL FINESTRUCTURE

(75) Inventors: Stefan Hell, Göttingen (DE); Volker Westphal, Hannover (DE); Norbert Quaas, Göttingen (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 75 days.

(21) Appl. No.: 11/861,405

(22) Filed: Sep. 26, 2007

(65) Prior Publication Data
US 2008/0007735 A1    Jan. 10, 2008

Related U.S. Application Data

(63) Continuation-in-part of application No. PCT/EP2006/002711, filed on Mar. 24, 2006.

(51) Int. Cl.
*G01B 11/24* (2006.01)
(52) U.S. Cl. ...................................... 356/601
(58) Field of Classification Search ......... 356/601–623, 356/317
See application file for complete search history.

(56) References Cited

U.S. PATENT DOCUMENTS

| | | | |
|---|---|---|---|
| 5,254,477 A | 10/1993 | Walt | |
| 6,259,104 B1 | 7/2001 | Baer | |
| 7,253,893 B2 | 8/2007 | Hell et al. | |
| 2007/0003958 A1* | 1/2007 | Okamoto et al. | 435/6 |
| 2008/0018891 A1* | 1/2008 | Hell et al. | 356/317 |

FOREIGN PATENT DOCUMENTS

| DE | 101 54 699 A1 | 5/2003 |
|---|---|---|
| WO | WO 2006/103025 A1 * | 10/2006 |

OTHER PUBLICATIONS

Hell, Stefan W., "Toward Fluorescence Nanoscopy", Nature Biotechnology, vol. 21, No. 11, Nov. 2003, pp. 1347-1355.

* cited by examiner

*Primary Examiner*—Hoa Q Pham
(74) *Attorney, Agent, or Firm*—Thomas, Kayden, Horstemeyer & Risley, LLP

(57) ABSTRACT

A method of microscopically examining a spatial fine structure comprises the steps of selecting a luminophore from the group of luminophores which have two physical states, the two states differing from each other with regard to the luminescence properties displayed by the luminophore, and which are reversibly, but essentially completely transferable out of one into the other state of their two states by means of an optical signal; overlaying a surface of the spatial fine structure with the luminophore; and determining the profile of the surface overlaid with the luminophore. The step of determining the profile of the surface comprises the sub-steps of transferring the luminophore by means of the optical signal out of the one into the other of its two states outside a presently observed measurement point, measuring luminescence light emitted by the luminophore, and repeating the sub-steps of transferring and measuring for further measurement points distributed over the surface.

13 Claims, 2 Drawing Sheets

METHOD OF MICROSCOPICALLY EXAMINING A SPATIAL FINESTRUCTURE

CROSS REFERENCE TO RELATED APPLICATIONS

This application is a continuation in part of International Patent Application PCT/EP2006/002711 entitled "Verfahren zur mikroskopischen Untersuchung einer räumlichen Feinstruktur", filed on Mar. 24, 2006, and claiming priority to co-pending German Patent Application No. DE 10 2005 013 969.8 also entitled "Verfahren zur mikroskopischen Untersuchung einer räumlichen Feinstruktur" filed Mar. 26, 2005.

FIELD OF THE INVENTION

The invention generally relates to a method of microscopically examining a spatial fine structure. More particularly, the comprising the invention relates to a method of microscopically examining a spatial fine structure, the method comprising the steps of coating a surface of the spatial fine structure with an auxiliary agent, and microscopically determining the profile of the surface coated with the auxiliary agent.

The fine structure can be an artificial, i.e. a man-made fine structure. For example, the spatial fine structure can be generated by a lithographic process.

Generally, the fine structures examined according to the present description are microstructures and nanostructures, i.e. structures having detail dimensions in the micrometer and nanometer range.

BACKGROUND OF THE INVENTION

A known method of microscopically examining a spatial fine structure is applied in the production of electronic semiconductor devices for checking conductor fine structures or isolator fine structures. Here, the respective fine structure is metallised with aluminium, for example, and then electron-microscopically examined. Electron-microscopy is used to spatially resolve the fine structure as far as possible. However, the efforts to be taken for electron-microscopic examination are high. The object having the fine structure has to be locked in a high vacuum apparatus already for metallization with the oxidation-sensitive aluminium; electron-microscopic examination can always only be executed in high vacuum. This means that no volatile matters may be emitted by the fine structure, which could deteriorate the high vacuum and/or damage the high vacuum apparatus. The efforts for installation and use of an electron-microscope itself are also quite high. Additionally, it has to be regarded as a disadvantage that the fine structures which have been examined electron-microscopically have to be discarded because of their irreversible coating with aluminium. I.e. the known method cannot be applied to check a fine structure which is as such also present in a final product. Instead, it is only possible to take lost samples.

At present, very few alternatives to electron-microscopic examination are available in the lithographic production of fine structures, if a resolution in the range of less than 150 nm is to be obtained. Present printed circuit board tracks in microelectronics already comprise widths down to 90 nm with even lower track distances. The recognisable alternatives to electron-microscopy are methods in which the fine structure to be examined is scanned with a probe. Atomic Force Microscopy (AFM) and Scanning Near Field Optical Microscopy (SNOM) belong to these methods, which on the one hand need no high vacuum, but which are on the other hand dependent on an exact and thus laborious adjustment of the clean fine structure with regard to the sensible arrangement for moving the respective probe, and which are thus extremely slow as compared to the size of the fine structure to be examined. The efforts to be taken for microscopic examination according to the known methods thus seem to be significantly reducible only in that very few samples of the fine structures generated lithographically are examined. This, however, essentially increases the danger of faultily produced electric devices.

A method of fluorescence-microscopically examining a sample is for example known from U.S. Pat. No. 7,253,893. A fluorescence dye, by which structures of interest within a sample have been dyed in a previous step, is at first transferred into an excited energetic state by means of an exciting optical signal. In this optical excitation the usual limit of $\lambda/(2n \sin\alpha)$ for spatial resolution in optical methods applies, $\lambda$ being the wavelength of the light used, n being the refraction index of the sample, and $\alpha$ being the half aperture angle of the objective used. To get below this limit, the optically excited state of the fluorescence dye is de-excited again with a de-exciting optical signal outside a desired measurement point in which the de-exciting optical signal has a zero point; i.e. the fluorescence dye in the sample is forced to stimulated emission everywhere outside the measurement point by means of the optical signal. The dimensions of the resulting still fluorescent measurement point, i.e. the spatial resolution of the remaining fluorescence can be lowered clearly below the usual optical resolution limit in that the de-exciting optical signal is applied to the sample outside the desired measuring point at such an intensity, that a saturation in de-excitation by stimulated emission is achieved. Thus, the fluorescence dye in the sample only remains in the excited state in a strongly delimited area about the zero point of the intensity distribution of the de-exciting optical signal and can only fluoresce in this area.

According to Hell, Nature Biotech., 21, 1347-1355. the size of the fluorescent measuring point $\Delta x$ and thus the resolution follows $\Delta x \approx \lambda/(2n \sin \alpha \sqrt{(I/I_s)})$, $\lambda$ being the wavelength of the de-exciting optical signal, n being the refraction index of the sample, $\alpha$ being the half aperture angle of the objective used, I being the applied intensity of the de-exciting optical signal, and $I_s$ being the saturation intensity. The saturation intensity $I_s$ is the characteristic intensity at which the fluorescence dye in the sample can be de-excited by application of the de-excitation optical signal by 50% from a statistics point of view.

SUMMARY OF THE INVENTION

The present invention relates to a method of microscopically examining a spatial fine structure, the method comprising the steps of selecting a luminophore from the group of luminophores which have two physical states, the two states differing from each other with regard to the luminescence properties displayed by the luminophore, and which are reversibly, but essentially completely transferable out of one into the other state of their two states by means of an optical signal; overlaying a surface of the spatial fine structure with the luminophore; and determining the profile of the surface overlaid with the luminophore; wherein the step of determining the profile of the surface comprises the sub-steps of: transferring the luminophore by means of the optical signal out of the one into the other of its two states outside a presently observed measurement point, measuring luminescence light emitted by the luminophore, and repeating the sub-steps of transferring and measuring for further measurement points distributed over the surface.

More particular the present invention relates to method of microscopically examining a spatial fine structure, the method comprising the steps of selecting a fluorescence dye from the group of fluorescence dyes which have two physical states comprised of an active state in which the fluorescence dyes emit fluorescence light and an inactive state in which the fluorescence dyes do not emit fluorescence light, and which are reversibly, but essentially completely transferable out of the active into the inactive state by means of an optical signal; overlaying a surface of the spatial fine structure with the fluorescence dye; and determining the profile of the surface overlaid with the fluorescence dye; wherein the step of determining the profile of the surface comprises the sub-steps of transferring the fluorescence dye by means of the optical signal out of its active state into its inactive state outside a presently observed measurement point, the optical signal being applied to the luminophore at such an intensity that a transfer of the fluorescence dye out of its active state into its inactive state is saturated, measuring luminescence light emitted by the luminophore, the luminescent light emitted by the luminophore originating out of the presently observed measurement point only, and repeating the sub-steps of transferring and measuring for further measurement points distributed over the surface.

In the new method, a luminophore is used as an auxiliary agent for microscopically examining a spatial fine structure, the luminophore having two states which differ from each other with regard to the luminescence properties of the luminophphore. Further, the luminophore can be reversibly, but essentially completely transferred out of the one into the other state by means of an optical signal. Luminescence light emitted by the luminophore is measured for determining the profile of the surface previously overlaid with the luminophore, the luminophore being transferred into the other of its two states in the surrounding of each presently observed measurement point.

Particularly but not exclusively, fluorescence dyes are suited as a luminophore for use in the new method. The physical process behind the luminescence of the luminophore is not essential; it needs not to be fluorescence. If, in the following, more detailed reference is made to a fluorescence dye as an example of the luminophore for use in the new method, this is not to be understood in such a way any statements made in this context do only apply to a fluorescence dye. Instead, the term fluorescence dye is to be understood as a synonym of the term luminophore as far as nothing different results from the particular context. The same applies to fluorescence light as an example of luminescence light.

Luminescence light which is emitted by the luminophore is measured in the new method to the end of microscopically examining the spatial fine structure. I.e. it is a procedure, which may also be termed luminescence microscopy. In the following, as a particular example, reference will be made to fluorescence microscopy, the same applying here as above with regard to the fluorescence dye as an example of the luminophore: the term fluorescence microscopy or fluorescence microscopically examining is to be understood here as a synonym for measuring the luminescence light from the luminophore with spatial resolution, so far as nothing different results from the particular context.

In fluorescence microscopy different measures are known for increasing the spatial resolution to such an extent that it is sufficient for the examination of artificial fine structures which are of commercial interest at present and in the foreseeable future. For example a so-called confocal arrangement and a multi-photo excitation of the fluorescence dye may be considered in fluorescence microscopy to enhance the spatial allocation of the detected or produced fluorescence light to a particular measurement point. In the new method, such measures can also be applied.

In any case of the new method, however, the luminophore will be selected in such a way that it has two states, which differ from each other with regard to their luminescence properties, the luminophore being reversibly, but essentially completely transferable out of its one into its other state by means of an optical signal. Thus, it becomes possible, to transfer the luminophore outside a spatially delimited area the dimensions of which get below the usual limit of the spatial resolution in optical methods of $\lambda/(2n \sin \alpha)$ into a state in which the luminescence properties of the luminophore differ from those within the spatially delimited area. This allows for measuring the luminescence light emitted by the luminophore with a spatial resolution of better than $\lambda/(2n \sin \alpha)$, $\lambda$ being the wavelength of the optical signal used for transferring the luminophore from the one state into the other state.

The transfer of the luminophore from its one state into its other state can be regarded as essentially complete, if at least 80%, preferably at least 90%, more preferable at least 96% and most preferably at least 99% of the luminophore are transferred into the other state.

Particularly, in measuring the luminescence light, the luminophore can be transferred into an inactive state, in which it does not emit luminescence light, except of the presently observed measurement points. If this is accomplished by means of a transfer between the states of the luminophore which is driven up to saturation, the excitation of the transfer only having a zero point at the presently observed measurement, a quite considerable increase of the spatial resolution in measuring the luminescence light can be achieved.

Particularly, the luminophore can be transferred out of its previously excited state into an inactive state except of the presently observed measurement points so that it only remains in the excited states within the presently observed measurement points, and detected luminescence light can only origin from these presently observed measurement points. The same result is achieved, if the fluorescence dye is transferred into a state which is not luminescent at all everywhere outside the presently observed measurement points.

An increased spatial resolution is also possible by means of an inverse transfer of the luminophore into an active state everywhere outside the presently observed measurement points. The signal of interest having the increased spatial resolution then is the reduced or even completely missing luminescence light out of the presently observed measurement points.

In the new method, the surface of the fine structure can be coated with the luminophore at a surface concentration between $10^8$ mm$^{-2}$ and $10^{15}$ mm$^{-2}$, preferably at a surface concentration of $10^{11}$ mm$^{-2}$ and $10^{12}$ mm$^{-2}$. These dimensionless values indicate the surface concentrations of the luminescent centres of the luminophore. With a usual luminophore consisting of single molecules which each have one luminescent centre, the surface concentrations indicate the number of the molecules per 1 mm$^2$ surface area. The preferred range of the surface concentration of $10^{11}$ to $10^{12}$ mm$^{-2}$ approximately corresponds to a monolayer of a typical fluorescence dye used as a luminophore with a typical molecule size of 0.5 to 2 nm. Already at this surface concentration, the luminophores begin to tend to transfer their latent energy to adjacent luminophore molecules instead of emitting luminescence light. I.e. an even higher surface concentration of the luminophore does not necessarily result in an increase of the detectable emission of fluorescence light. It is, however, a reserve of luminophore molecules, which is activated, if the luminophore is bleached, i.e. activated as an undesired side-effect of the influence of the optical signal by which it is transferable between its one into its other state, and/or of the excitation light by which it is excited into its excited state out of which it emits fluorescence light. Such a bleaching can also have other causes and is a usual property of luminophores, the consequences of which can be obviated, however, by means of an excess of luminophore at the surface of the fine structure to such an extent that in measuring the luminescence light from the luminophore the interesting profile of the surface can be determined with high spatial resolution over long periods of time.

The surface of the fine structure can, for example, be overlaid with the luminophore by means of vapour-deposition. It is also possible that the luminophore is, for example, applied to the surface with a carrier liquid and that this carrier liquid is afterwards evaporated leaving the luminophore on the surface. It is not required that the luminophore covers the surface of the fine structure uniformly. The luminophore may, for example, be present on the overlaid structure at a higher concentration in protruding areas of the structure than in depressions of the structure. The luminophore may also adhere differently to different materials of the structure. In any case, the spatial distribution of the liminophore will indicate the spatial contour, i. e. the profile of the structure overlaid with the luminophore.

The new method can be applied in the production of various artificial fine structures. The fine structure can be a fine structure which is as such present in a final product, like for example in microelectronics. Thus, the fine structure can, for example, directly form conductive tracks. The fine structure, however, can also be a temporary structure, like for example a mask which is afterwards used for the manufacture of a further complementary fine structure, and which is then removed so that it is as such no longer present in the respective final product.

A particular field of application of the new method is the lithographic production of spatial fine structures. Here, one starts with a radiation-sensitive material, and for actually generating the fine structure a layer of the material is deposited on a substrate, the deposited layer is irradiated in spatially defined areas, and the irradiated layer is developed, parts of the layer being removed and the desired fine structure remaining. Upon developing the layer, its irradiated or its not-irradiated spatial areas may be removed.

The radiation-sensitive material can, for example, be sensitive to UV-radiation and/or X-rays and/or electron radiation, one of these kinds of radiation being used for irradiating the deposited layer in the spatially defined areas.

When the lithographic production of fine structures is mentioned here, particular reference is made to a photo-lithographic process. The more general term without the constituent "photo", however, is deliberately used here to explicitly not exclude the use of an electron beam or any other particle beam for irradiating the radiation-sensitive material, which would not fall under the general term of photo-lithography.

A particular advantage of the new method is that the luminophore can be removed from the surface of the fine structure after determining the profile of the surface of the spatial fine structure marked with the luminophore. Thus, the examined fine structure can be processed into a final structure. In other words, the new method can be applied to a fine structure which can as such be found in an actual final product. Depending on the kind of the fine structure it may be further processed without removing the luminophore, if the luminophore does not disturb further processing of the fine structure; or the luminophore may purposefully be bleached if it does not matter in further processing the fine structure, provided that it is inactivated in this way.

For example, the luminophore can be washed off the fine structure with a washing solution. This washing solution is to be selected so that it takes off the luminophore, for example, by dissolving it particularly well, but leaves the fine structure under the luminophore unaffected.

In microscopically examining the fine structure, the luminescence light emitted by the luminophore can advantageously be imaged on a detector using an immersion objective. Microscopic examination of the layer on basis of the luminescence light does not require a difference in refraction indices between the fine structure and the adjacent medium. The fine structure in the layer is not directly imaged, i.e. not imaged as such in the new method. Instead the spatial distribution of the luminescence light emitted by the luminophor is captured allowing interference on the fine structure. By using an immersion objective in combination with an immersion medium, the refraction index of which is as close to the refraction index of the fine structure as possible, optimum optical conditions for a high spatial resolution are provided.

Most advantageously, a solid body is used as the immersion objective in the new method to avoid any danger to already take the luminophore off the surface of the fine structure with an immersion liquid. Particularly, the solid body serving as the immersion medium can be a so-called solid immersion lens. In contact with the surface of the fine structure covered with the luminophore a solid immersion lens has a sufficient depth of field across the profile of the fine structure, to capture the distribution of the luminophore in this direction of depth with a sufficiently high spatial resolution.

The new method does completely without introducing the fine structure in a high vacuum apparatus. Thus, it provides excellent conditions for microscopically examining a high number of fine structures at acceptable efforts. In measuring the luminescence light emitted by the luminophore the resolution increasing methods described here allow for spatial resolutions by which even periodic line structures of 80 nm width and 40 nm distance or even finer design can be analysed with luminescence light and optical signals in the visible range.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
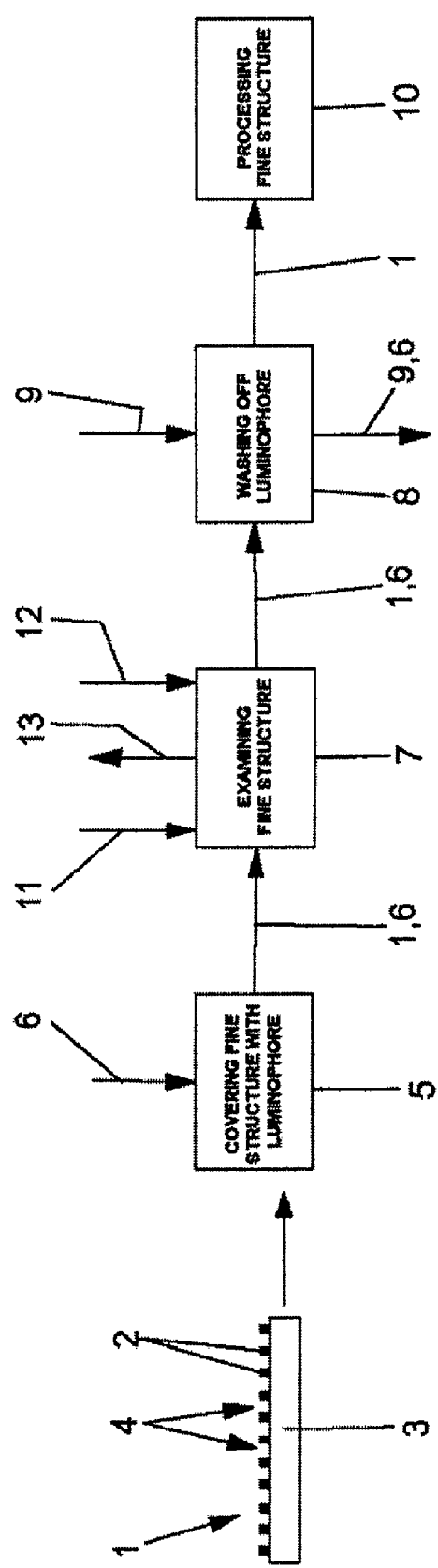
FIG. 1 is a block diagram illustrating the new method.

Referring now in greater detail to the drawings, FIG. 1 outlines a method of microscopically examining a spatial fine structure 1, which is indicated as a pattern of line-shaped elevations 2 above a substrate 3. The fine structure 1 can be the result of a lithographic process which is not described in further detail here. In a first method step 5 the surface 4 of the fine structure 1 is overlaid with a luminophore 6 which enables its microscopic examination. To this end, the luminophore 6 is evaporated so that it is uniformly deposited on the surface 4. In a next method step 7, the fine structure 1 covered with the luminophore 6 is microscopically examined. Here, the luminophore 6 which is a fluorescence dye is excited by a beam of excitation light 11 for fluorescence, but de-excitated again by a beam of de-excitation light 12 through stimulated emission except of in the present measurement points of interest. Thus, only fluorescence light 13 which originates from the remaining excited areas about the present measurement points of interest is measured. In a method step 8 following the method step 7 of microscopically examining, the luminophore 6 is washed off the fine structure 1 with a washing solution. The fine structure 1 cleaned from the luminophore 6 can be further processed in a following method step 10 without any damage being caused by the previously executed method steps 5, 7 and 8.

Figure 2:
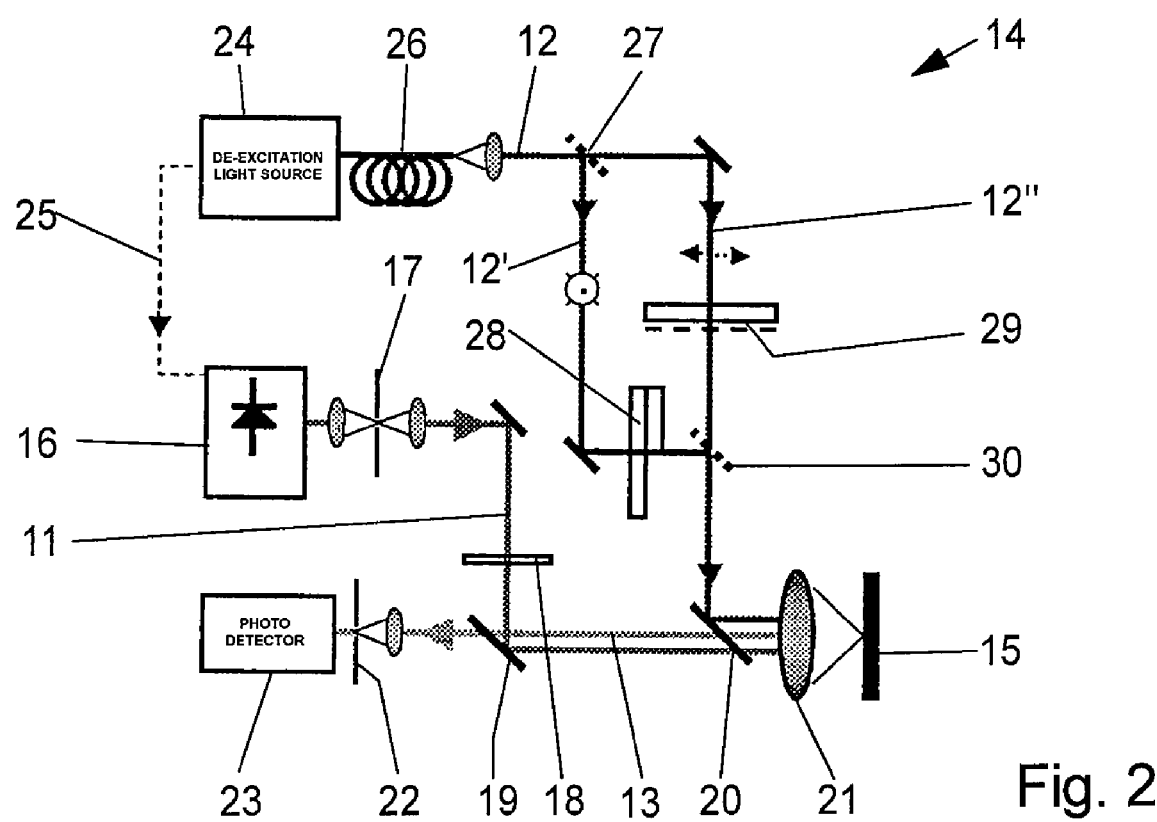
FIG. 2 shows the principle design of a fluorescence microscope to be used in the method according to FIG. 1.

FIG. 2 shows the principle design of a fluorescence microscope 14, which can be used in the method outlined in FIG. 1. The fluorescence microscope 14 has an excitation light source 16 for exciting the fluorescence dye in the sample 15, which is a pulsed laser diode (PicoQuant GmbH, Germany) emitting the beam of excitation light 11 at a wavelength of 635 nm in pulses of 68 ps with a repetition rate of 80 MHz. Emitted by the excitation light source 16, the beam of excitation light 11 is guided through a pinhole 17 and then gets through a λ/4-plate which results in the beam of excitation light 11 being circularly polarised. After deflection at a dichroitic mirror 19 the beam of excitation light 11 gets through a further dichroitic mirror 20, into an objective 21 and is then focussed in the sample 15 by the objective 21. The objective 21 is a solid body immersion objective. The dichroitic mirrors 19 and 20 and further filters which are not depicted here are adjusted to the wavelength of the beam of excitation light 11 of 635 nm and to an emission range of the fluorescence dye in the sample 15 of 650 to 710 nm, these being the characteristics of the xanthene fluorescence dye JA 26. The fluorescence light 13 from the sample is captured by the objective 21 and imaged onto a pinhole 22 in front of a photo detector 23. The pinhole 22 is confocally arranged with regard to the pinhole 17 in the optical path of the beam of excitation light 11. The pinhole 22 and the photo-detector 23 can be realised by means of a light guide fibre which guides the light to a counting avalanche photodiode. Here, the core diameter of the light guide fibre may correspond to the 0.7-fold diameter of the Airy-disk upon imaging the diameter of the light guide fibre into the focal plane of the objective 21.

The design of a confocal fluorescence microscope is augmented by the following elements to obtain a STED-fluorescence microscope, the dichroitic mirror 20 already belonging to this augmentation. In a STED-microscope, the dimensions of the volume in which the fluorescence dye is still excited so that it can emit fluorescence light are reduced everywhere outside a measuring point of interest by depleting the exited state of the fluorescence dye by means of stimulated emission (STimulated Emission Depletion). To provide the corresponding de-excitation light 12, the fluorescence microscope 14 has a de-excitation light source 24 which is a Ti-saphire laser (Mai Tai, Spectra Physics), which is phase-coupled in the femtosecond range, which emits the beam of excitation light 12 at a wavelength of 780 nm, and which also provides a clock for the excitation light source 16 via a trigger signal 25, here. The red-shifted pulses emitted by the de-excitation light source 24 are guided through a single mode fibre of 100 m length to stretch them up to a pulse duration of 300 ps. Thus, the pulses of the beam of de-excitation light 12 are considerably longer than those of the excitation beam of light 11 of $\epsilon$ps. In this way, an undesired excitation of the fluorescence dye which is not de-excited again is avoided. The single mode fibre 26 does not affect the polarisation of the beam of de-excitation light 12, which is afterwards split into partial beams 12' und 12" having orthogonal s- and p-polarisation by means of a polarising beam splitter 27. After passing through phase plates 28 and 29, which adjust the polarisation of the partial beams 12' and 12" with regard to each other, the partial beams 12' and 12" are superimposed by means of a further polarising beam splitter 30 in such a way, that the beam of de-excitation light 12 which is imaged by the objective 21 in the sample 15 forms a torus-shaped area around the beam direction having an intensity higher than 0. This interference pattern has a minimum, i.e. an intensity of 0, in the centre of the torus-shaped area. In this central area, the excitation of the fluorescence dye in the sample 15 is not de-excited again by means of the beam of de-excitation light 11, whereas everywhere outside the central area a de-excitation occurs by means of the beam of de-excitation light 12. In this way, the lateral resolution of the fluorescence microscope 14 can be lowered below the diffraction limit of the beam of excitation light 11 used for exciting the sample. By means of a corresponding intensity distribution of the beam of de-excitation light along the beam direction with intensities higher than sero in front of and behind the measurement point of interest, the depth resolution of the fluorescence microscope 14 may also be lowered. Details of these measures can be taken from WO 02/084265 which is incorporated herein by reference.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of microscopically examining a spatial fine structure, the method comprising the steps of:
   selecting a luminophore from the group of luminophores
      which have two physical states, the two states differing from each other with regard to the luminescence properties displayed by the luminophore, and
      which are reversibly, but essentially completely transferable out of one into the other state of their two states by means of an optical signal;
   overlaying a surface of the spatial fine structure with the luminophore; and
   determining the profile of the surface overlaid with the luminophore;
   wherein the step of determining the profile of the surface comprises the sub-steps of:
      transferring the luminophore by means of the optical signal out of the one into the other of its two states outside a presently observed measurement point,
      measuring luminescence light emitted by the luminophore, and
      repeating the sub-steps of transferring and measuring for further measurement points distributed over the surface.

2. The method of claim 1, wherein the sub-step of transferring includes applying the optical signal to the luminophore at such an intensity that a transfer of the luminophore out of the one into the other of its two states is saturated.

3. The method of claim 1, wherein the step of selecting includes selecting the luminophore from the group of luminophores in which the other of their two states is an inactive state in which they do not emit luminescence light, and wherein the sub-step of transferring includes transferring the luminophore into its inactive state outside the presently observed measurement point so that, in the step of measuring, the luminescent light emitted by the luminophore originates out of the presently observed measurement point only.

4. The method of claim 3, wherein the step of selecting includes selecting the luminophore from the group of fluorescence dyes.

5. The method of claim 3, wherein the sub-step of transferring includes transferring the luminophore into the inactive state by means of stimulated emission.

6. The method of claim 1, wherein the step of overlaying includes overlaying the surface of the fine structure with the luminophore at a surface concentration in the range of $10^8$ mm$^{-2}$ to $10^{15}$ mm$^{-2}$.

7. The method of claim 6, wherein the step of overlaying includes overlaying the surface of the fine structure with the luminophore at a surface concentration in the range of $10^{11}$ mm$^{-2}$ to $10^{12}$ mm$^{-2}$.

8. The method of claim 1, wherein the step of overlaying includes overlaying the surface of the fine structure with the luminophore by means of vapour deposition.

9. The method of claim 1, further comprising, after the step of determining, the step of removing the luminophore from the surface of the fine.

10. The method of claim 9, wherein the step of removing includes washing the luminophore off the surface with a washing solution.

11. The method of claim 1, wherein the step of measuring includes imaging the luminescence light emitted by the luminophore onto a detector by means of an immersion objective.

12. The method of claim 11, wherein the step of measuring includes using a solid immersion lens as an immersion medium in combination with the immersion objective.

13. A method of microscopically examining a spatial fine structure, the method comprising the steps of:
- selecting a fluorescence dye from the group of fluorescence dyes
  - which have two physical states comprised of an active state in which the fluorescence dyes emit fluorescence light and an inactive state in which the fluorescence dyes do not emit fluorescence light, and
  - which are reversibly, but essentially completely transferable out of the active into the inactive state by means of an optical signal;
- overlaying a surface of the spatial fine structure with the fluorescence dye; and
- determining the profile of the surface overlaid with the fluorescence dye;
- wherein the step of determining the profile of the surface comprises the sub-steps of:
  - transferring the fluorescence dye by means of the optical signal out of its active state into its inactive state outside a presently observed measurement point, the optical signal being applied to the luminophore at such an intensity that a transfer of the fluorescence dye out of its active state into its inactive state is saturated,
  - measuring luminescence light emitted by the luminophore, the luminescent light emitted by the luminophore originating out of the presently observed measurement point only, and
  - repeating the sub-steps of transferring and measuring for further measurement points distributed over the surface.

* * * * *